United States Patent [19]

Calcagno et al.

[11] 3,985,794

[45] *Oct. 12, 1976

[54] PROCESS FOR THE PRODUCTION OF VINYL ACETATE FROM ETHYLENE

[75] Inventors: Benedetto Calcagno, Milan; Claudio Divo, Saronno (Varese); Marcello Ghirga, Bresso (Milan), all of Italy

[73] Assignee: Societa' Italiana Resine S.I.R. S.p.A., Milan, Italy

[ * ] Notice: The portion of the term of this patent subsequent to Mar. 23, 1993, has been disclaimed.

[22] Filed: Oct. 1, 1969

[21] Appl. No.: 862,914

[30] Foreign Application Priority Data

Oct. 12, 1968  Italy .................................. 22416/68

[52] U.S. Cl. ............................. 260/497 A; 204/123; 204/149
[51] Int. Cl.² ........................................... C07C 67/05
[58] Field of Search .......... 260/497 A; 204/10, 109, 204/111

[56] References Cited
UNITED STATES PATENTS

| | | | |
|---|---|---|---|
| 1,982,160 | 11/1934 | Guinot | 260/531 R X |
| 3,346,624 | 10/1967 | Shaeffer et al. | 260/497 A |
| 3,420,873 | 1/1969 | Olivier | 260/497 A |
| 3,427,237 | 2/1969 | Morris | 204/10 X |
| 3,459,644 | 8/1969 | MacClean | 260/604 R X |
| 3,461,157 | 8/1969 | Olivier et al. | 260/497 A |
| 3,492,340 | 1/1970 | Aguilo et al. | 260/497 A |
| 3,534,087 | 10/1970 | Leftin et al. | 260/497 A X |

FOREIGN PATENTS OR APPLICATIONS

| | | | |
|---|---|---|---|
| 40-11,367 | 6/1965 | Japan | 260/497 A |
| 1,088,203 | 10/1967 | United Kingdom | 260/497 A |

OTHER PUBLICATIONS

Luder et al. *General Chemistry* 3rd ed. Sanders (1965) pp. 192–193.
Perry, *Chemical Eng'rs Handbook* 4th ed., McGraw Hill (1963) 19–22; 19–23.

*Primary Examiner*—Lorraine A. Weinberger
*Assistant Examiner*—Michael Shippen
*Attorney, Agent, or Firm*—Sughrue, Rothwell, Mion, Zinn and Macpeak

[57] ABSTRACT

Palladium and copper ethylene-oxidation catalysts, used in production of vinyl acetate, are regenerated by a process including electrolytic deposition of the metals and subsequent reconversion to halides.

6 Claims, No Drawings

PROCESS FOR THE PRODUCTION OF VINYL ACETATE FROM ETHYLENE

The present invention relates to a process for the production of vinyl acetate from ethylene.

As is well known, vinyl acetate can be produced by bringing ethylene and oxygen into contact with a palladium salt in an environment containing acetic acid, in the presence of a copper salt and a salt of acetic acid that is ionised under the conditions of reaction.

It is also known that as the reaction of converting ethylene into vinyl acetate proceeds, a diminution in the activity of the catalyst is observed.

This phenomenon, which becomes more and more evident as time passes, results in a steady reduction in the mean specific production of vinyl acetate, which falls to levels below what is commercially acceptable. This phenomenon of continually falling specific production also creates awkward problems in the running of the entire plant.

For good progress and satisfactory operation in the reaction whereby vinyl acetate is formed from ethylene, there is obviously a need for maintaining the activity of the catalytic substance at values which are sufficiently high and which remain as far as possible constant with time.

To that end, it has been customary hitherto for the catalytic substance, once its activity has been reduced, to be subjected to combustion after withdrawal from the reaction vessel and separation from the acetic acid solution. This results in a solid mass consisting for the most part of oxides and chlorides of the metals composing the catalytic mixture, along with smaller amounts of those metals in their elementary form.

This substance is then treated with acetic acid and hydrochloric acid, so as to regenerate the catalytic mixture, which is then returned to the reaction vessel in which the vinyl acetate is being produced.

The process described above, however, has a number of serious drawbacks, because of the complexity of the equipment required, the marked corrosive action due to the substance treated and to the high temperatures used, and the inevitable losses arising, for example, from the volatility of copper salts and from the carrying away of material in the combustion gases.

It has now been discovered that the drawbacks associated with the techniques known hitherto for the production of vinyl acetate by the catalytic oxidation of ethylene in the presence of acetic acid can be avoided or reduced if the catalytic mixture, when its activity is reduced, is removed from the reaction vessel in which the vinyl acetate is being produced and — containing as it does ions of palladium, copper, alkali metal or alkaline earth metal, and chlorine or other halogen in acetic acid solution — is subjected to an electrolytic deposition process enabling the palladium and copper to be recovered almost entirely in their elementary form. The metallic palladium and copper thus recovered are converted into the corresponding chlorides, which are fed once more to the reaction vessel in which the vinyl acetate is being produced.

The invention is hereafter described in terms of the use of alkali metals and chlorides in the catalytic mixture.

More specifically, in accordance with the present invention in preferred form, the catalytic mixture of reduced activity is removed from the vessel in which the vinyl acetate is being produced, continuously or at pre-determined intervals, and transferred to an electrolytic cell equipped with electrodes separated by porous baffles in which the pores have a mean diameter of about 1 micron.

The catalytic mixture removed from the vessel in which the vinyl acetate is produced is introduced into the cathode compartment, whereas the anode compartment receives a dilute acidic solution, preferably an aqueous solution of hydrochloric acid, the level of which should preferably be maintained above the cathodic level.

The cathode and anode compartments should also preferably be hermetically separated above the levels of the liquids, to avoid possible intermingling of the gases evolved at the electrodes.

Preferably in the present invention, the electrolysis is carried out at a cathode current density of between 0.1 and 10 A./sq.dm. and preferably between 0.5 and 6 A./sq.dm., preferably with automatic control of cathode potential if a high current output is desired. The potential difference between the electrodes, for one and the same current density, depends in particular on the type of equipment used, the type and shape of electrodes, the concentration of the ions in solution, the working conditions and the need for depositing the copper and palladium at the cathode without at the same time liberating substantial amounts of hydrogen thereon. The cell temperature should preferably be maintained at between 60° and 90° C., though satisfactory results can be obtained outside those limits. The electrolysis of the catalytic mixture is continued until deposition of the metallic palladium and copper on the cathode is substantially complete. The solution from which the copper and palladium have been separated can be fed into a column of ion exchange resin of strong acid type in the acid form, in which, apart from possible traces of copper ions, the alkalimetal ions are held back. The effluent from the ion exchange column, consisting in the main of a mixture of acetic acid and water, is sent for recovery — by distillation, for example — of the acetic acid.

The ions held back by the column of resin, mainly alkali metal ions with small amounts of copper ions, are removed by one of the processes normally used for the purpose, such as with an acid solution, for example, and preferably a dilute solution of hydrochloric acid.

The conversion of the metallic palladium and copper recovered electrolytically to the corresponding chlorides should preferably be carried out after the metals have been placed in suspension in a dilute aqueous solution of hydrochloric acid. In one of the preferred forms of the present invention, the metallic palladium and copper are placed in suspension in the effluent obtained by the treatment with dilute hydrochloric acid of the column of ion exchange resins and hence containing not only free hydrochloric acid, but also alkali metal chloride and possibly small amounts of copper chloride.

Chlorine gas is bubbled into the resultant suspension, in a suitable container maintained preferably at ambient temperature.

This produces an aqueous solution of chlorides of the various metals, palladium, copper and alkali metal from which the dissolved chlorine is removed, for example, by blowing in air.

Alternatively, conversion may be carried out by bubbling either air or oxygen into the hydrochloric acid suspension of metallic palladium and copper, preferably maintained at ambient temperature, in which condition dissolution appears to be more rapid.

The solution thus formed, containing substantially all the copper, palladium and alkali metal ions, removed from the reaction vessel for regeneration, is fed back to the vessel for the production of vinyl acetate along with acetic acid.

Normally, in the production of vinyl acetate from ethylene, ethylene and oxygen or an oxygen-containing gas are fed separately or mixed, with an ethylene/oxygen molar ratio of between 10:1 and 25:1 and preferably between 14:1 and 22:1, preferably at a pressure of between 20 and 50 atm., into a reaction vessel kept at a temperature of between 80° and 160° C. and preferably between 100° and 140° C. containing from 0.5 to 5 gramme-ions/liter of an alkaline metal, 0.01 to 0.5 gramme-ions/liter of copper, 0.0002 to 0.02 gramme-ions/liter of palladium and 0.1 to 1 gramme-ion/liter of chlorine in acetic solution.

When the catalytic mixture is regenerated by the process here proposed and the foregoing operating procedure is adhered to, the yield of vinyl acetate is high and to all intents and purposes constant with time.

EXAMPLE 1

In a reaction vessel containing a catalytic mixture consisting of 408 g. of copper ion, 5.2 g. of palladium ion and 700 g. of lithium ion, dissolved in 70 liters of acetic acid solution, a gaseous mixture consisting of 90% of ethylene, 5% of oxygen, 4% of carbon dioxide and 1% of nitrogen was re-cycled at the rate of 200 cu.m.N/hour.

The working pressure was maintained at 30 atm. and the temperature at 120° C.

Also fed continuously into the reaction vessel were a solution of acetic acid at the rate of about 25 liters an hour and hydrochloric acid sufficient to keep the chlorine ion concentration in the vessel at 0.2 gramme-ion/liter. The mean specific production during the first 100 hours, expressed in mols of ethylene converted into acetate and acetaldehyde, was equivalent to 1.2 mols per liter of catalytic mixture per hour.

The mean specific production then dropped with time and was equivalent in the 200th hour to about 0.7 mol of ethylene converted per liter of catalytic mixture per hour.

At that point, the catalytic solution was removed from the vessel in which the vinyl acetate was being produced and was introduced into a system consisting of an electrolytic cell with a frusto-conical bottom in communication with a decanting vessel through which, with the aid of an outside pump, it was possible to effect continuous re-cycling of the liquid from what vessel to the cell. The electrolytic cell was provided with a central cathode and two side anodes made from sheet graphite. Two porous aluminium silicate baffles having pores with a mean diameter of 1 micron, interposed between the cathode and the anodes, divided the cell into one cathode compartment and two anode compartments.

The catalytic mixture removed from the vinyl acetate production vessel was introduced into the cathode compartment and also filled the decanting vessel; into the anode compartments was fed a 1% dilute solution of hydrochloric acid, the level of which was maintained a few centimeters above that of the cathode liquid. The cathode and anode compartments were also hermetically separated above the level of the liquids, so as to avoid possible intermingling of the gases evolved at the electrodes.

The solution in the cathode compartment was maintained at 80° C. by a suitable thermostat arrangement and the current feed to the cell was switched on, the electrode potential being controlled so as to avoid any significant discharge of hydrogen at any time.

Palladium and copper were deposited on the face of the cathode in the form of a barely cohesive agglomerate, which became detached by the action of its own weight and the movement of the solution recirculated. The detached metal deposit entered the decanting vessel together with the solution, where it settled on the bottom, the solution being re-cycled to the cell.

Electrolysis was interrupted when the concentration of the copper in solution had fallen to 0.092 g/liter and that of the palladium to negligible values, corresponding to the deposition of more than 98% of the copper and approximately 100% of the palladium initially present. The cathode solution was then discharged and passed into a column of DOWEX-50 resin in the free acid form. The liquid effluent minus cations and the water from the subsequent washing of the column were sent for distillation, for recovery of the acetic acid.

The column of ion exchange resin was then regenerated in acid form by washing with an aqueous solution of 10% hydrochloric acid and gave an effluent consisting of a solution of lithium chloride, free hydrochloric acid and traces of copper chloride. This solution and the deposit of metallic palladium and copper obtained electrolytically were introduced into a suitable container maintained at ambient temperature, in which a constant stream of air kept the solid in suspension and oxidised it.

When no metal remained in suspension in the liquid, the solution, containing $PdCl_2$, $CuCl_2$ and $LiCl$, in a quantity substantially identical to that of the initial fresh catalytic solution, was fed, together with acetic acid (some of it recovered, to the reaction vessel in which vinyl acetate was being produced, where, in the same conditions as initially, it gave a mean specfic production, expressed in mols of ethylene converted into vinyl acetate and acetaldehyde, equivalent to 1.2 mols per liter of catalytic mixture per hour.

EXAMPLE 2

In a reaction vessel containing a catalytic mixture consisting of 415 g. of copper ion, 6.0 g. of palladium ion and 2,450 g. of sodium ion, dissolved in 70 liters of an acetic solution, a gaseous mixture consisting of ethylene (85%), oxygen (5%), carbon dioxide (5%) and inert gases (5%) was recycled at the rate of 200 N.cu.m/hour. The working pressure was maintained at 30 atm. and the temperature at 120° C.

A solution of acetic acid was fed continuously to the reaction vessel at the rate of 25 liters/hour, as well as sufficient hydrochloric acid to maintain the chlorine ion concentration therein at 0.3 gramme-ions/liter.

Catalytic mixture was drawn off from the vessel at the rate of 1 liter/hour continuously and transferred to an electrolytic cell for treatment as described in Example 1.

The metal deposit of copper and palladium in powder form, obtained by electrolysis of the catalytic mixture withdrawn from the reaction vessel, was placed in suspension in the effluent obtained from regeneration in the ion exchange column with the aqueous solution of HCl and treated with chlorine gas at ambient temperature. This dissolved to give a solution of palladium and copper chlorides.

A quantity of this solution such as to contain approx. 5.9 g. of copper ion and approx. 0.082 g. of palladium ion received an addition of 89 g. of sodium chloride and was fed continuously every hour to the reaction vessel in which the vinyl acetate was being produced.

The procedure described was adopted for a run of one month, during which the mean specific production, expressed in mols of ethylene converted into vinyl acetate and acetaldehyde, remained at values lying between 1.05 and 0.95 mols per liter of catalytic mixture per hour.

We claim:
1. In the process for the production of vinyl acetate from ethylene, which comprises uniting ethylene and oxygen or oxygen-containing gases in the presence of a catalytic mixture consisting essentially of palladium and copper halogenides and an acetate being a member selected from the group consisting of alkali metal and alkaline earth metal acetates in acetic acid, at high temperature and pressure, the improvement which comprises:
   a. removing the catalytic mixture from the reaction vessel in which the vinyl acetate is being produced,
   b. subjecting said mixture to an electrolytic deposition process in which the catalytic mixture removed from said vessel is transferred for electrolytic deposition to the cathode compartment of an electrolytic cell in which the electrodes are separated by porous baffles, while a dilute acid solution is introduced into the anode compartment, said palladium and copper being recovered substantially in their elementary form,
   c. said metallic palladium and copper being placed in suspension in a dilute aqueous solution of hydrochloric acid and converted into their respective chloride salts by bubbling a member selected from the group consisting of chloride gas, air, and oxygen gas into said suspension, and
   d. feeding the thus formed palladium and copper chloride salts back to the reaction vessel in which the vinyl acetate is being produced,
   said electrolytic deposition being carried out at a cathode current density ranging from 0.1 to 10.0 A./sq.dm., and
   the temperature during the electrolytic deposition ranging from 60° to 90° C.

2. The process of claim 1, in which the current density ranges from 0.5 to 6.0 A./sq.dm.

3. The process of claim 1, wherein the electrolytic solution from which the copper and palladium have been separated, is passed through a column containing an ion exchange resin of the strong acid type, which serves to retain the alkali or alkaline earth metal ions, while the effluent is permitted to recover the acetic acid.

4. The process of claim 1, wherein vinyl acetate is produced by the feeding of ethylene and a member selected from the group consisting of oxygen or an oxygen-containing gas, with an ethylene/oxygen molar ratio ranging from 10:1 to 25:1 into a reaction vessel maintained at a temperature of from 80° to 160° C, and further containing from 0.5 to 5.0 gram-ions per liter of alkali metal, from 0.0002 to 0.2 gram-ions per liter of palladium, from 0.01 to 0.5 gram-ions per liter of copper, and from 0.1 to 1.0 gram-ions per liter of chlorine ion in an acetic acid solution.

5. The process of claim 4, wherein said ethylene/oxygen molar ratio ranges from 14:1 to 22:1, the temperature ranging from 100° to 140° C, and the pressure ranging from 20 to 50 atmospheres.

6. The process of claim 5, wherein said temperature ranges from 80° to 160° C.

* * * * *